United States Patent [19]
Mikhail et al.

[11] Patent Number: 6,050,934
[45] Date of Patent: Apr. 18, 2000

[54] URINARY CATHETER HAVING PALPITATABLE DISCHARGE VALVE WITH PROTECTIVE SHOULDERS

[75] Inventors: Adel A. Mikhail, Bloomington; Gene E. Stobbs, Brooklyn Park; Adel M. Hashw, Eden Prairie; Shelley N. Johnson, Minnetonka, all of Minn.

[73] Assignee: CV Dynamics, Inc., Inver Grove Heights, Minn.

[21] Appl. No.: 09/030,132

[22] Filed: Feb. 25, 1998

Related U.S. Application Data

[60] Provisional application No. 60/036,294, Feb. 26, 1997.

[51] Int. Cl.⁷ ...................................................... A61F 2/00
[52] U.S. Cl. ...................................... 600/30; 128/DIG. 25
[58] Field of Search ............... 600/29–31; 128/DIG. 25; 604/96–104, 174, 256, 247, 349, 329, 54, 55, 93, 246, 250; 251/342; 137/849

[56] References Cited

U.S. PATENT DOCUMENTS

| | | |
|---|---|---|
| 3,331,371 | 7/1967 | Rocchi et al. . |
| 3,459,175 | 8/1969 | Miller . |
| 3,503,400 | 3/1970 | Osthagen et al. . |
| 3,841,304 | 10/1974 | Jones . |
| 3,967,645 | 7/1976 | Gregory . |
| 4,026,298 | 5/1977 | Grausz . |
| 4,346,714 | 8/1982 | Child . |
| 4,432,757 | 2/1984 | Davis, Jr. . |
| 4,553,959 | 11/1985 | Hickey et al. . |
| 4,587,954 | 5/1986 | Haber . |
| 4,643,169 | 2/1987 | Koss et al. . |
| 4,846,784 | 7/1989 | Haber . |
| 4,932,938 | 6/1990 | Goldberg et al. . |
| 4,946,449 | 8/1990 | Davis, Jr. . |
| 4,968,294 | 11/1990 | Salama . |
| 5,078,676 | 1/1992 | Bailly . |
| 5,090,424 | 2/1992 | Simon et al. . |
| 5,114,398 | 5/1992 | Trick et al. . |
| 5,131,906 | 7/1992 | Chen . |
| 5,169,393 | 12/1992 | Moorehead et al. . |
| 5,234,409 | 8/1993 | Goldberg et al. . |
| 5,306,226 | 4/1994 | Salama . |
| 5,330,437 | 7/1994 | Durman . |
| 5,624,395 | 4/1997 | Mikhail et al. .............................. 600/29 |
| 5,707,357 | 1/1998 | Mikhail et al. .............................. 604/96 |

*Primary Examiner*—John P. Lacyk
*Attorney, Agent, or Firm*—Moore and Hansen

[57] ABSTRACT

An indwelling urinary catheter having a palpitatable multi-axial dome-type discharge valve with protective shoulders. The protective shoulders are preferably raised above other unprotected portions of an outer surface of the valve. In preferred embodiments, the valve wall is made substantially of a first material and each of the protective shoulders include an elongated thickness of a second material which is more rigid than the first material. The valve has a peripheral trough to maximize drainage. Valve openings traverse an arcuate pathway, and adjacent valve elements are separated by an intermediate rib to ensure a reliable closure.

25 Claims, 6 Drawing Sheets

URINARY CATHETER HAVING PALPITATABLE DISCHARGE VALVE WITH PROTECTIVE SHOULDERS

CROSS-REFERENCE TO RELATED APPLICATIONS

The present application claims the benefit of prior filed, co-pending provisional application Serial No. 60/036,294 filed Feb. 26, 1997.

This application is also related to U.S. patent application Ser. No. 08/392,529 filed Feb. 23, 1995, and now abandoned; and U.S. patent application Ser. Nos. 08/546,572 filed Oct. 20, 1995, now issued as U.S. Pat. No. 5,624,395, and U.S. Ser. No. 08/605,435 filed Feb. 22, 1996 now issued as U.S. Pat. No. 5,707,357. Each of the aforementioned applications is hereby incorporated herein by reference.

BACKGROUND OF THE INVENTION

1. Field of Invention

This invention relates generally to discharge valves for managing urinary incontinence and retention, preferably discharge valves associated with intra-urethral or "indwelling" Foley-type urinary catheters, the valve being an externally preferably located multi-axial palpitatable discharge valve and having protective shoulders to minimize inadvertent placement of force on the valve which is sufficient to unintentionally open the valve and release retained urine.

2. Prior Art

The field of urinary catheters has long been dominated by the Foley-type catheter, which is well known in the art and comprises an inflatable balloon for disposition within a patient's bladder and a discharge or drainage tube which extends from the bladder, through the urethra, to the exterior when the catheter is in place within the patient. The Foley-type catheter provides passive urinary drainage, and the ability to clamp the catheter closed at a location exterior of the patient. Representative examples of Foley-type catheters are shown in U.S. Pat. Nos. 4,055,187; 4,154,243; 4,188,954; and 4,335,723 to Patel.

Foley-type catheters have many drawbacks. These drawbacks include, among other things, relatively high intra-urethral leakage rates, the inability to selectively control discharge, and the diminution in the patient's mobility or physical activities due to the constant need for a drainage collection device interconnected to the open catheter.

Many attempts have been directed towards solving these problems, and the prior art reflects that many basic improvements have been adopted and combined in a variety of forms to optimize the function of the particular catheters. However, practical, reliable, and commercially viable alternatives are still needed.

One alternative provides a releasable connection between the Foley-type catheter and the external drainage tube to enhance mobility, as shown in U.S. Pat. No. 4,955,858 to Drews. A check valve can also be disposed at a point along the catheter or drainage tube as shown in U.S. Pat. No. 3,967,645 to Gregory. However, these improvements do not address other problems such as an intra-urethral leakage, and have not resulted in a solution that is satisfactory for most patients.

The use of an inflatable balloon or other blocking device to minimize intra-urethral leakage around the exterior of the catheter, and valves disposed within the catheter body to permit selective voiding, are considered fundamental advances in the art. Early examples of developments along these lines include U.S. Pat. No. 3,841,304 to Jones and U.S. Pat. No. 3,503,400 to Osthagen. A blocking device comprising a hydrogel collar disposed around the catheter tube of a Foley-type catheter is disclosed. The collar is designed to slide axially along the catheter tube into contact with the body at the distal end of the urethra to hold the balloon in sealing contact with the neck and orifice of the bladder. The collar also provides an additional obstacle to leakage at the distal end of the urethra.

Valves contained within catheters that can be manipulated by bending, flexing, or extending the catheter are shown in U.S. Pat. No. 4,822,333 to Lavareene; and U.S. Pat. Nos. 4,432,757 and 4,350,161 to Davis. These catheters are generally unsuitable for use by female patients, and are subject to leakage resulting from normal body movement when used in male patients.

Collapsible- or restricted-lumen catheters that have predetermined release pressure thresholds have also been disclosed. However, these catheters are subject to leakage, do not drain completely, and have predetermined operational pressure ranges which may not be appropriate for a large number of patients without undue experimentation particularly when determining a safe high end limit to the range. In addition, the relatively short distance between the orifice of the bladder and the distal end of the urethra in female patients limits the suitability of some designs that require an extended length of lumen to maintain the requisite pressure threshold. Representative examples of such designs are shown in U.S. Pat. No. 4,553,959 to Hickey and U.S. Pat. No. 3,672,372 to Heimlich.

U.S. Pat. No. 5,234,409 to Goldberg; U.S. Pat. No. 5,114,398 to Trick; and U.S. Pat. No. 5,030,199 to Barwick show representative examples of valved catheters designed for female patients. These catheters incorporate a variety of valves and actuators which illustrate some of the inherent obstacles in designing catheters for female patients, namely providing a manipulable or palpitatable valve that can be located and gripped by the patient without presenting a hygienic risk or being inconvenient for the patient to operate.

Intra-urethral plug-type devices have also been disclosed. These devices include palpitatable or manually activated valves for selective control over voiding. They are generally retained within the distal end of the patient's urethra using inflatable bulbs, radial serrations, or regions of enlarged diameter, and generally include an exposed portion that permits selective activation of the valve or periodic removal of the device. Representative examples of such devices are shown in U.S. Pat. No. 5,131,906 to Chen; U.S. Pat. No. 5,090,424 to Simon; U.S. Pat. No. 4,968,294 to Salama; U.S. Pat. No. 4,457,299 to Cornwall; and U.S. Pat. No. 3,768,102 to Kwan-Gett.

A wide variety of discharge valve designs have been contemplated for use with urinary catheters. These valves are usually actuated mechanically, but may also be actuated magnetically or by other means. The more prevalent types of mechanical valves include ball-and-seat, duckbill, inflatable check, plug, and dome-type valves. These valves may all be operated manually by the patient, however, some types of valves are identified as "palpitatable" based upon a portion of the valve being squeezed or pressed in order to open the valve. The palpitatable valve may be disposed internally or externally for male patients, although internal valves may be more difficult to use, uncomfortable, and unreliable. The palpitatable valve must be located externally for a female patient. Palpitatable discharge valves may also be classified as orientation-dependent (uniaxial) or orientation-independent (multi-axial), based upon whether pressure must be applied to a pair of selected points or surfaces in order to open the valve sufficiently for normal discharge operation, or whether the valve will open when pressure is exerted radially from any two opposing directions.

These basic types of mechanical, inflatable, and palpitatable valve configurations are displayed in U.S. Pat. No. 5,306,226 to Salama; U.S. Pat. Nos. 5,269,770 and 5,261,896 to Conway; U.S. Pat. Nos. 4,946,449 to Davis; U.S. Pat. No. 4,932,938 to Goldberg; U.S. Pat. No. 4,846,784 and 4,813,935 to Haber; and U.S. Pat. No. 4,643,169 to Kross, as well as several other references previously discussed. Representative examples of magnetically-actuated valves are shown in U.S. Pat. No. 5,041,092 to Barwick and U.S. Pat. No. 4,731,670 to Loe.

The Davis '449, Goldberg '938, and Haber '794 patents disclose several types of palpitatable valves that may be disposed internally or externally. A uniaxial duckbill valve may be rotated between the user's fingers until pressure is directed on the proper sites to maximize fluid flow, but the rotational torque can cause irritation, inflammation, and leakage. The Goldberg '938 patent teaches a tactile sensing means for determining the proper orientation of a duckbill valve to ensure complete opening, however properly orienting the catheter and valve upon initial insertion still requires time and training. In addition, the Davis '449 and Goldberg '938 patents both disclose dome-type valves that operate substantially the same as uniaxial duckbill valves. These dome-type valves similarly provide two opposing valve elements, but the slit or cut forming the valve opening approaches or intersects the side wall of the valve at a point below or downstream of the apex of the dome. While this configuration provides enhanced drainage capabilities for small aliquots of fluid remaining within the valve body compared with conventional duckbill valves, the proximity of the ends of the slit to the side wall of the catheter body restricts the amount that the valve can be opened in the region nearest the side wall (and therefore the lowest or most downstream portion of the valve) and risks nicking or scoring the side wall of the valve when the slit is cut. One alternative shown in the Davis '449 patent appears as a separate dome-shaped valve piece that is cut and inserted within the catheter body, which does not eliminate the restriction on the width of the valve opening adjacent the side wall of the valve body, and requires additional time, labor, costs, and quality control measures to accommodate the additional manufacturing steps.

The Davis '449 patent further shows a drainage tube connector being inserted through the dome-type valve to hold the valve in an open position. Similarly, U.S. Pat. No. 3,421,509 to Fiore discloses a protective sleeve for a urinary catheter having several overlapping wedge-shaped flap elements that are opened by insertion of a drainage tube connector.

The Haber '784 patent discloses another valve design similar in longitudinal cross section to a duckbill valve, wherein the valve elements are lobes having extended contact surfaces that present a central lumen when pressure is applied, rather than conventional blade-type elements that pivot apart when the valve is deformed.

The use of duckbill valves having pivotal blade elements or dome-type valves having single or cross-shaped slits are generally preferred for palpitatable valves. However, existing catheter designs having palpitatable valves do not provide as reliable a closure under normal pressures as is generally desired. In addition, the valves do not adequately drain small aliquots of urine from within the valve, thereby fostering a highly infectious environment located in close proximity to contamination from the outside environment and a pathway for ready transmission of bacteria infection to the bladder.

Another problem associated with palpitatable valves is that the slightest force inadvertently exerted on the right place or places can open the valve allowing urine to flow. For instance, force can be placed on an external valve if it is pressed between a patient's legs when their legs are crossed. If so, urine can be released and the patient can be embarrassed by the unintended failure of the catheter valve to retain the urine. Furthermore, many of the valves are difficult to operate and require much more force to operate that is easily mustered by some elderly patients. Therefore, providing a valve which requires a reduced amount of force from the patient to operate, at the time that protection is provided to help minimize inadvertent or unintended operation of the valve resulting in the unintended release of urine.

In view of the many shortcomings and patient dissatisfaction with existing designs for urinary discharge valves, Applicants have developed a preferred urinary discharge valve design intended to meet the needs and desires of the majority of male and female patients suffering from incontinence or urinary retention disorders.

BRIEF SUMMARY OF THE INVENTION

The present invention provides an indwelling urinary catheter having a palpitatable multi-axial discharge valve with protective shoulders. The discharge valve has a valve body including a valve wall defining an outer surface and an inner surface. The discharge valve further includes a valve membrane having an upper surface and a lower surface, the valve membrane having a plurality of valve openings and an outer edge or periphery connected with the inner surface of the valve wall. Each of the plurality of valve openings have both a closed and an open position, such that the patient can selectively manipulate the valve so that at least one of the plurality of openings can be open from a closed position and closed from an open position. The outer surface of the valve includes a plurality of protective shoulders which provide structural support to the valve wall such that each of the valve openings can remain in the closed position when a force is applied to the outer surface of the valve wall proximate any of the plurality of protective shoulders, which force would be sufficient to manipulate the valve such that at least one of the valve openings would be open from a closed position if the force was applied to an unprotected portion of the valve wall. In preferred embodiments, the protective shoulders are raised above the unprotected portions of the outer surface of the valve wall. In preferred embodiments the valve wall and the valve membrane are substantially made of first material which is a flexible polymeric material which can be deformed such that the valve openings can be opened from a closed position when sufficient force is applied to the valve wall to deform the valve membrane, wherein the valve opening will generally return to the closed position from the open position when the force is no longer applied. In such embodiments, the valve wall preferably includes an elongated thickness of a second material proximate each of the plurality of protective shoulders. The second material is more rigid than the first material, such that the second material is more resistant to deformation than the first material.

It is an object of the present invention to provide a catheter having a palpitatable discharge valve which provides a measured of portion protection against accidental opening of one of the valve openings due to the unintended application of a force to the outer surface of the valve wall.

It is a further object of the present invention to provide a valve membrane which is interconnected with the valve wall in such a way that it provides an active hinge mechanism for easy manipulation of the valve so that elderly patients may easily manipulate the valve to void urine retained in the patient's bladder.

It is further object of this invention to design an indwelling urinary catheter system of the type having: (1) a catheter body disposed within the urethra of the patient for extended periods of time, (2) a palpitatable valve that may be selectively manipulated by the patient for voiding urine, and (3) an inflatable balloon disposed within the bladder to minimize intra-urethral leakage along the exterior of the catheter.

It is a related object of this invention to fabricate the above urinary catheter system using a process that optimizes the uniformity and reliability of the catheters.

It is another object of this invention to design the above urinary catheter system so as to incorporate a multi-axial palpitatable discharge valve which may be conveniently operated by male and female patients.

It is a related object of this invention to design the multi-axial valve such that it consistently provides a reliable closure at both low or high fluid pressures, drains completely at low or negligible fluid pressures, and permits the passage of a drainage tube connector for extended use by immobile or incapacitated patients.

It is an additional object of this invention to fabricate the above multi-axial valve using a method that enhances or enlarges the valve's seating or contact area compared with conventional duckbill or dome-type valves, and ensures that the valve elements consistently and reliably return to the proper closed configuration.

It is yet another object of this invention to design the urinary catheter system such that it may be readily adjusted to match the particular anatomical characteristics of a patient and will remain configured as adjusted, and in particular accommodates continuous incremental adjustments of the catheter length for female patients.

It is a further object of this invention to design the above urinary catheter such that the valve may be disposed externally of the patient, and wherein the exterior shape of the valve body reduces the potential for inadvertent or accidental deformation of the valve due to contact or pressure with the patient's clothing or legs, and further provides a rapid and secure connection for a drainage tube that maintains the valve in an open position.

It is yet another object of this invention to provide the above urinary catheter with the capability to adjust the pressure exerted on the inflatable balloon to a desired level to mitigate against dislodgement of the balloon from the neck and orifice of the bladder.

It is still another object of this invention to provide the above urinary catheter with a reservoir for the accumulation of an antiseptic gel to form a liquid seal against the egress of urine from the urethra, and a barrier against the ingress or migration of infectious contaminants, along the exterior of the catheter.

The urinary catheter of the present invention includes a catheter body disposed within the urethra of the patient for extended periods of time, a palpitatable valve that may be manipulated by the patient to selectively control voiding, and an inflatable balloon disposed within the patient's bladder to retain the catheter in position and minimize leakage along the exterior of the catheter. In one embodiment, the catheter body and tip are molded and a sleeve having a uniform thickness is sealed to the body to create the balloon. In another embodiment, the catheter body, tip, and balloon are molded as an integral unit using a synthetic material such as biologically compatible silicone in a manner that produces a substantially uniform balloon shape and symmetrical disposition relative to the catheter body. The balloon shape may be selectively altered by varying bonding patterns, wall thicknesses, or assembly characteristics.

The catheter body is preferably assembled with a molded discharge valve of the type disclosed herein. The palpitatable valve preferably includes a multi-axial dome-type construction with a peripheral trough surrounding the dome adjacent to and displaced slightly from the wall of the valve body. The peripheral trough maximizes drainage and permits a wider valve opening. In a preferred embodiment, each valve element is separated from adjacent valve elements by an intermediate rib, and the valve elements and intermediate ribs may be readily displaced radially from the longitudinal axis of the valve by insertion of a drainage tube connector. The valve elements are formed by cutting the dome while deformed to a flat configuration to create seating surfaces that are angled to increase their contact area. A retention collar may be positioned on a catheter body for female patients and may be adjusted axially along helical threads to exert a desired level of tension on the catheter body to maintain the base of the balloon in contact with the interior wall of the bladder adjacent the neck and orifice. The catheter and balloon may be fabricated using a bactericidal-containing synthetic resin, coated with bactericidal or friction-reducing agents, or the balloon may be inflated with a bactericide-treated fluid that permeates the balloon. An antiseptic gel coating the threaded portion of an alternate catheter accumulates on the proximal face of the retention collar and forms a fluid seal and barrier against migration of infectious contaminants along the exterior of the catheter, with a conical portion of the retention collar optionally being received within the distal orifice of the urethra. Many of these features are more fully described in the aforementioned U.S. patent applications which are incorporated herein by reference.

BRIEF DESCRIPTION OF THE DRAWINGS

In the drawings, in which like reference numerals refer generally to corresponding elements of the various embodiments throughout the several views.

DESCRIPTION OF THE PREFERRED EMBODIMENTS

Urinary catheters and palpitatable discharge valves of the present invention are generally shown in FIGS. 1–14 and generally referenced therein by the reference numeral 10.

Figure 1:
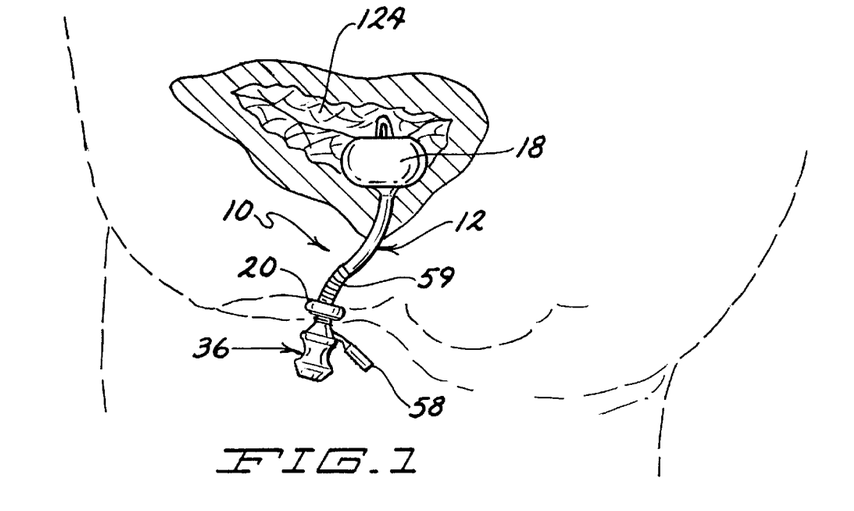
FIG. 1 is a partial anatomical side-sectional view of the urinary tract of a female patient showing a preferred catheter of the present invention implanted therein, the catheter having a palpitatable multi-axial discharge valve with protective shoulders a toroidal balloon and a retaining collar.
Figure 2:
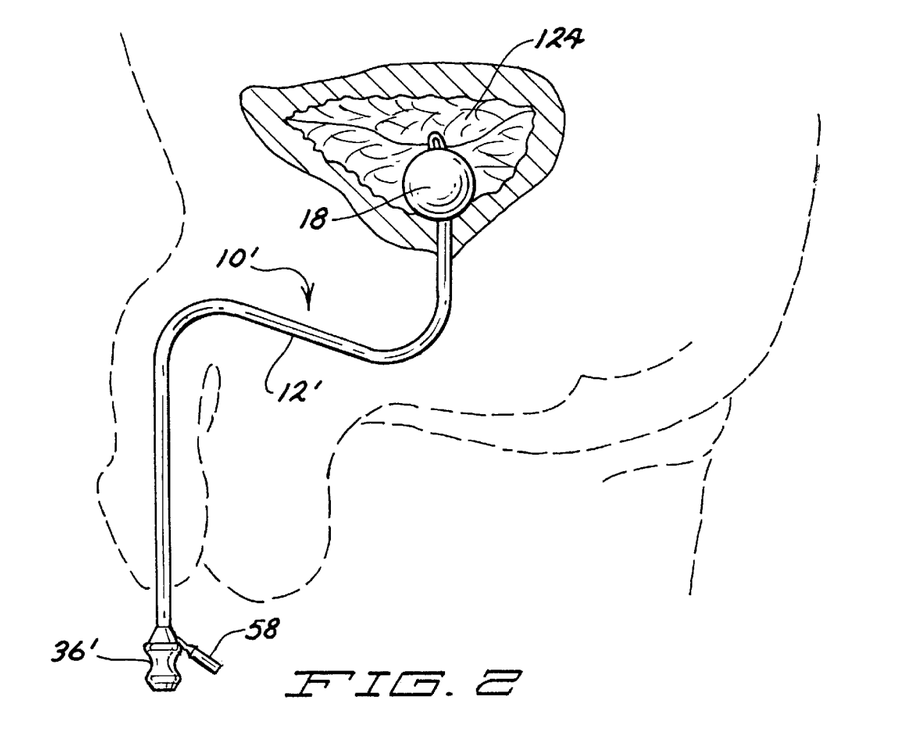
FIG. 2 is a partial anatomical side-sectional view of the urinary tract of a male patient generally showing an alternate catheter of the present invention implanted therein, the catheter having a similar valve to that shown in FIG. 1 and a generally spherical balloon.
Figure 3:
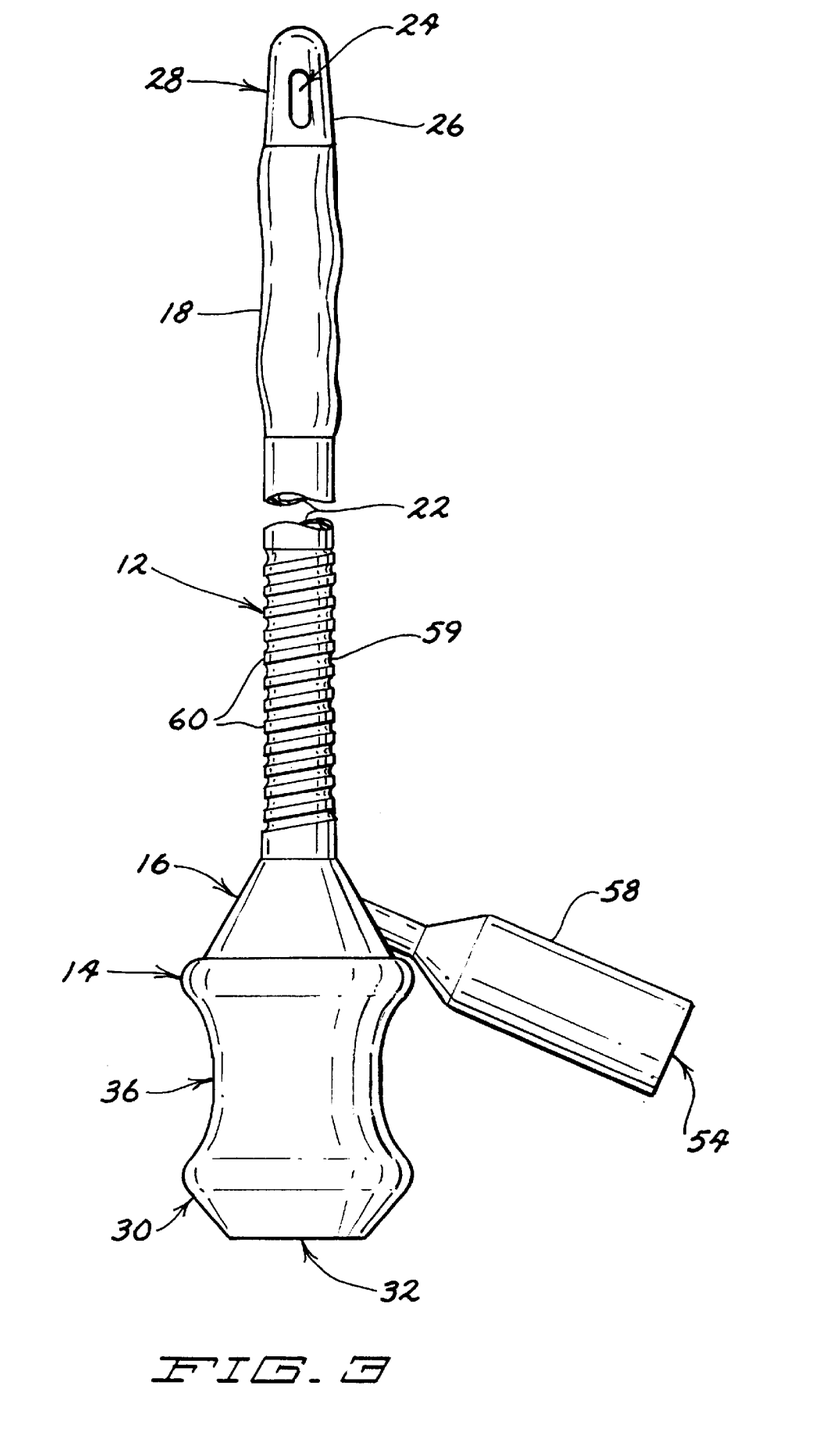
FIG. 3 is a side view of the catheter body of FIG. 1 including the preferred valve.

Referring now particularly to FIGS. 1–3, the illustrated catheters 10 and 10' includes a catheter body 12 that is composed of a distal portion 14 and a proximal portion 16 that are matingly connected as described below. An inflatable balloon 18 is connected to and extends from the catheter body 12, and a retention collar 20 is disposed around a threaded portion 59 of the catheter body 12.

The catheter body 12 defines a central lumen 22 extending from and communicating with Murphy Eye openings 24 through the side wall 26 of the catheter body 12, and a closely adjacent the proximal end 28 of the catheter body 12 to the distal end 30 of the catheter body 12 which defines a discharge opening 32. The proximal end 28 of the catheter body 12 preferably forms a partially enclosed and rounded tip of the catheter body 12, with the exception of the Murphy Eye openings 24 on the opposite sides of the catheter body 12. The catheter body 12 and central lumen 22 are further defined by a longitudinal axis (not shown) extending along the entire length of the catheter body 12, although the catheter body 12 may be freely flexed out of alignment with the longitudinal axis. Although a single opening 24 may also be utilized, including an opening (not shown) which intersects or overlaps the longitudinal axis at the tip of the catheter body, a plurality, preferably two openings 24, are preferred.

Now referring also to FIGS. 4–7 the distal portion 14 of the catheter body 12 defines a multi-axial palpitatable discharge valve or valve body 36, preferably including a dome-type valve member or membrane 38 that may be moved between a normally closed position to an open position when the valve body 36 is gripped and deformed, thereby deforming the valve membrane 38. The valve 36 can be deformed, in the manner shown in FIGS. 6 and 7, by applying squeezing pressure against any two opposing sides of the valve wall 40, which also forms the side wall of the distal portion 14 of the catheter body 12.

The valve wall 40 is generally cylindrical at its proximal end 41, and at its distal end 43 it preferably defines a truncated conical segment 42 terminating in the discharge opening 32. The proximal end of the distal portion 14 of the catheter body 12 defines an opening that permits the distal end of the proximal portion 16 to be matingly received within, and fixedly connected to, the proximal end of the distal 14 portion of the catheter body 12.

The illustrated inflatable balloon 18 is connected to, and molded unitarily with, so as to become a part of, the catheter body 12.

An inflation tube 52 defining an inflation lumen 53 within the catheter wall 26 extends from an opening 54 in the catheter wall 26, communicating with an interior inflation region (not shown) of the inflatable balloon 18, to an inflation port 58 interconnected to a proximal segment 56 of the inflation tube 52. Fluid is injected through the inflation port 58 and inflation lumen 53 to inflate the interior region of the inflatable balloon 18 and 18' from a completely collapsed configuration (shown in FIG. 3) to a completely inflated yet highly pliable or compliant configuration, which may be either a generally spherical shape as shown in FIG. 2, that is both radially and axially symmetrical, or conversely a toroidal or axially asymmetrical shape as shown in FIG. 1.

The catheter wall 26 defines helical threads 60 along a threaded 59 thereof, with the retention collar 20 defining mating threads (not shown) which permit the collar 20 to be turned in increments to move axially up or down the threaded portion 59 of the catheter body 12 by rotation of the collar 20 relative to the catheter body 12.

Figure 4:
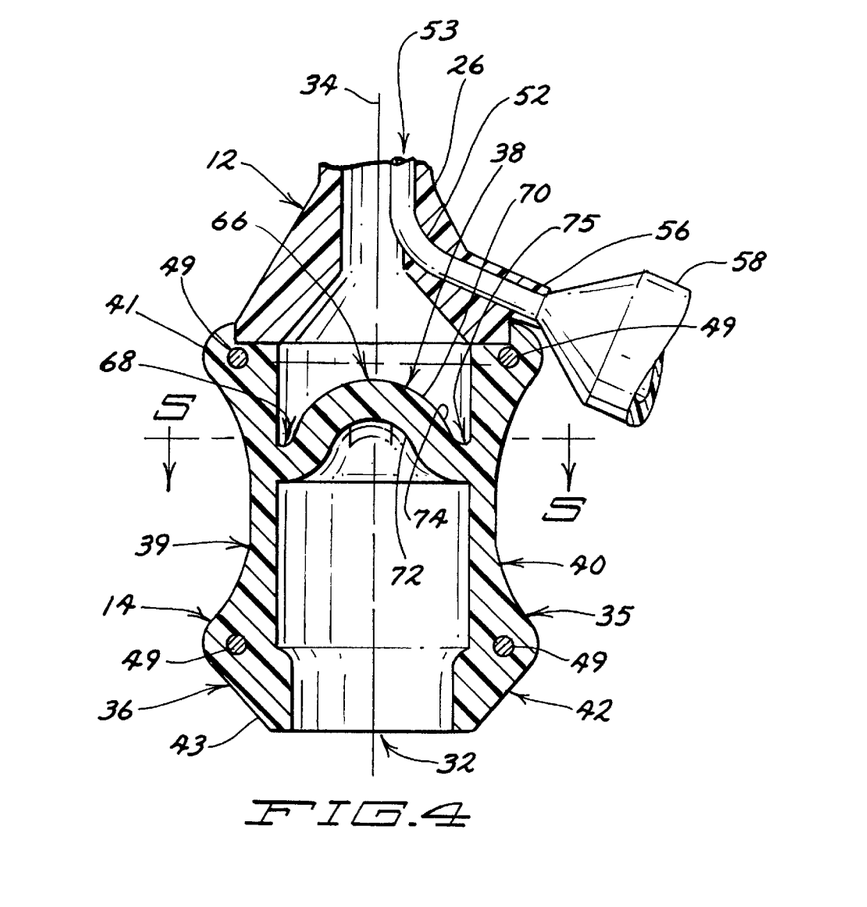
FIG. 4 is an enlarged partially broken away cross-sectional view of embodiment of the discharge valve of FIG. 1.
Figure 5:
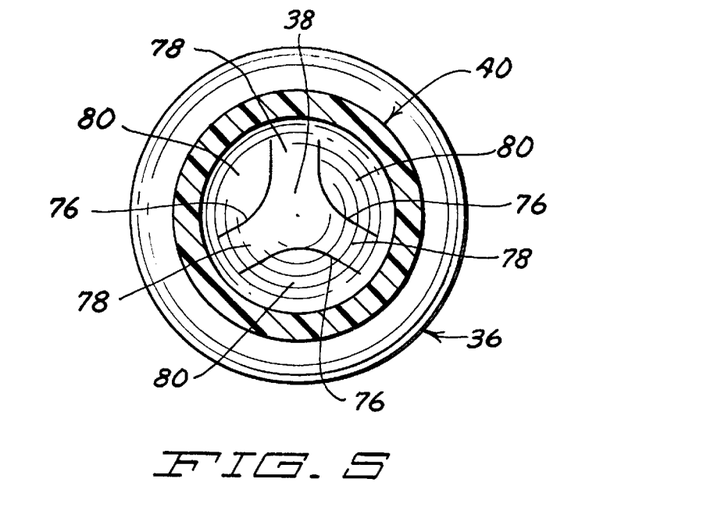
FIG. 5 is a cross-sectional view of the upper portion of the of FIG. 1, when the valve openings are closed as seen from the line 5—5 of FIG. 4.

Referring now particularly to FIGS. 4–7, a preferred embodiment of the dome-type multi-axial palpitatable discharge valve 36 is shown. The valve member or membrane 38 has a generally circular axial cross-section as shown in FIG. 5. The valve member 38 extends radially inward and slightly distally downward from the interior surface of the valve wall 40, and then further radially inward and generally proximally upward to an apex 66 intersecting a longitudinal axis 34, thereby forming a trough or intermediate region 68 circumscribing a generally arcuate central dome area, proximate the apex 66. The valve member having a convex surface 70 opposing the anticipated flow of fluid from the central lumen 22 and a concave surface 72 facing generally distally or downstream. The peripheral edge 74 of convex surface 70 differs from the convex surface 70 proximate the apex 66, because the convex surface 70 in the area of the peripheral edge 74 is in fact radially concave, creating a trough 75 which encircles the apex 66. In preferred embodiments to preformed inflation tube 52 and the catheter body are made of silicone rubber. A preferred inflation tube 52 is 80 durometer silicone rubber and the molded catheter body 12 is 50 durometer silicone rubber.

In order to minimize the unintended or unintentional releases of urine from the discharge valve 36 protective shoulders 37 at the distal and proximal ends of the preferred discharge valve 36 have been added to provide additional rigidity to minimize the likelihood that urine may be inadvertently released from the discharge valve 36 when the user accidentally places opposing forces on the valve wall 40. In the preferred embodiment, the protective shoulders 37 are raised above unprotected portions 39 of the outer surface 35 of the valve wall 40. In other embodiments (not shown), the protective shoulders need not be raised above the outer surface 35 proximate unprotected areas 39, so long as the protective shoulders 37 provide greater rigidity to the valve proximate the protective shoulders, as compared to the rigidity of the valve wall 40 proximate unprotected portions 39 of the valve wall 40. It will be appreciated that this can be accomplished by incorporating a harder or more rigid, material into the valve 36 proximate the protective shoulders.

For example, in the preferred embodiment of the discharge valve 36, the raised protective shoulders 37 which provide an increased amount of material proximate the raise shoulders 37, metal rings 49 are incorporated into the valve wall 40 proximate the raised protective shoulders 37 to provide further rigidity. These rings 49, can be made of any rigid metal, preferably stainless steel. Alternatively, the rings may be made of other materials which are more rigid than the material used to make the valve membrane 38 and the valve wall 40 of the valve or valve body 36. Preferably, the valve membrane 38 and the valve wall 40 are made of silicone rubber, or other flexible polymeric materials such as Kraton®, and the like, and preferably has a durometer value of about 12 to about 95 shore, preferably about 25 to about 60 shore, more preferably about 35 to about 45 shore, and most preferably about 40 shore. A second material will be used in preferred embodiments to reenforce the valve wall 40 proximate the protective shoulders 37. These materials will have a "hardness" or an increased durometer greater than that of the first material used to make the valve member 38 and the valve wall 40. In preferred embodiments the second material will have a durometer of at least 95 shore, preferably at least about 120 shore, more preferably at least about 130 shore. Polymeric material such as acrylics, polyvinalchorides (PVCs) and other polymeric materials having greater hardness then the silicone rubbers and other polymeric materials used to make the valve wall 40 and the valve membrane 38 will be suitable for this purpose. One product used in certain preferred embodiments is Delrin®. In alternate embodiments metals, fiberglass, and hardened glass may be used as well. In further alternate embodiments (not shown), a flat band of these hardened materials, which can encircle the valve or become incorporated within the valve, may be used to provide increased rigidity to protective shoulders (not shown) which are not raised above the outer surface 35 of the valve 36 proximate unprotected portions 39 of the valve wall 40.

The preferred discharge valve 36 shown in FIGS. 4–7 is made of silicone rubber having a durometer of 40 shore supported by stainless steal rings 49 which support raised protective shoulders 37 at the distal and proximal ends of the valve. The raised protective shoulders create a depression between these respective shoulders where an elder patient's thumb and forefinger may easily squeeze the valve 36 to open a valve opening or openings 76 in the valve membrane 38. The raised protective shoulders 37 effectively guide the user's fingers to the appropriate positions where force an be effectively applied to open the valve 36. These sites are designated by the open arrows 51 on either side of the valve 36 shown in FIG. 6. The protective shoulder 37 at the distal end of the valve body 36 also effectively provides a barrier preventing the user's fingers from sliding down along the valve wall 40 to the distal end proximate the discharge opening 32 where the user's fingers might become soiled by urine passing through the discharge opening 32.

Figure 6:
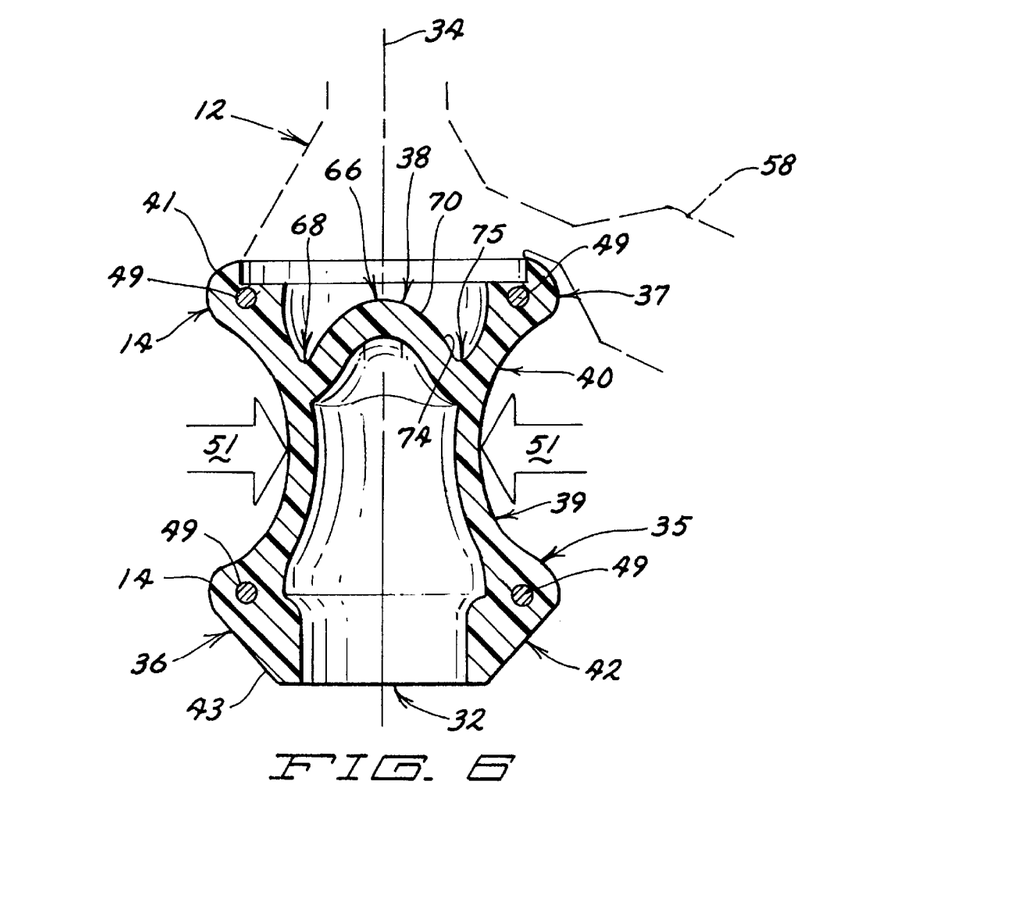
FIG. 6 is a side cross-sectional view of the body of the discharge valve shown in FIG. 1 when force, represented by the arrows, is applied to opposite sides of the valve body to deform the valve wall and the valve membrane, and open the valve.
Figure 8:
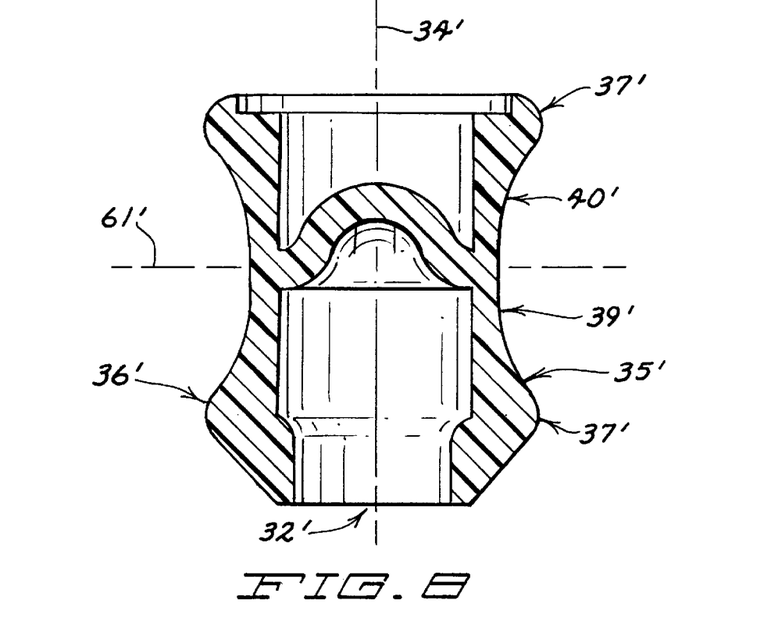
FIG. 8 is a cross-sectional view of an alternate valve body having raised protective shoulders which encircle a central lumen of the valve.

Referring now also to FIG. 8, a further alternate embodiment of the discharge valve 36' is shown. In this embodiment the protective shoulders 37' are raised above the outer surface 35' proximate the unprotected portion 39' of the outer wall 40'. However, no further supporting structure such as the rings provided in the embodiment shown in FIG. 6, are provided to prevent unintended manipulation of the valve 36' resulting in opening of the valve openings of the valve member 38'. Although the raised protective shoulders 37' do provide additional material to provide rigidity and prevent unintended valve opening events, it is likely that the durometer of the polymeric material used to make the valve body 36' will have to be at least somewhat higher than forty shore in order to avoid the unintended release of urine when the valve 36' is caught between a patient's legs or the leg, thereby applying force to opposite sides of the valve. Nevertheless, where is it is unnecessary to provide especially easily operable valve, such a valve may be especially suitable for its intended use.

Figure 9:
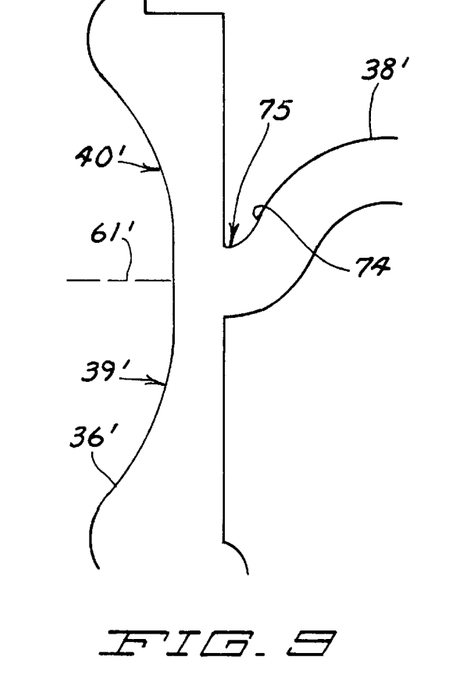
FIG. 9 is a diagrammatic view of a portion of a dome-type valve of the type shown in FIGS. 1–8; wherein the valve membrane is interconnected with the valve wall generally at a midpoint on the outer wall between the highest points of each of the two raised protective shoulders.
Figure 10:
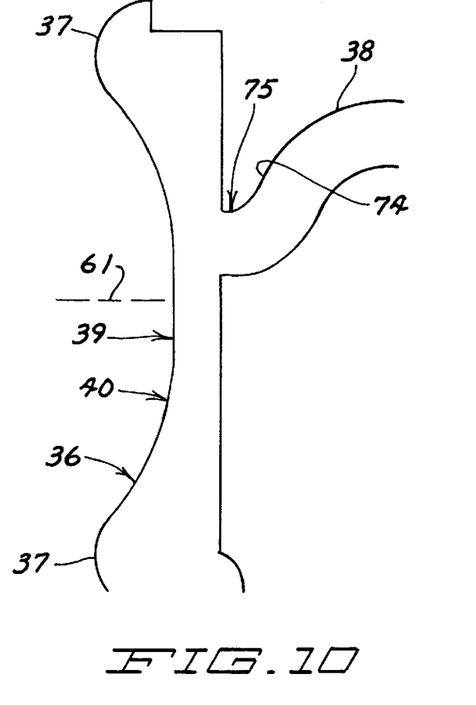
FIG. 10 is a diagrammatic view another alternate embodiment similar to that shown in FIG. 9, wherein; the interconnection between the valve membrane and the valve wall is removed from the midpoint indicated from FIG. 9.
Figure 11:
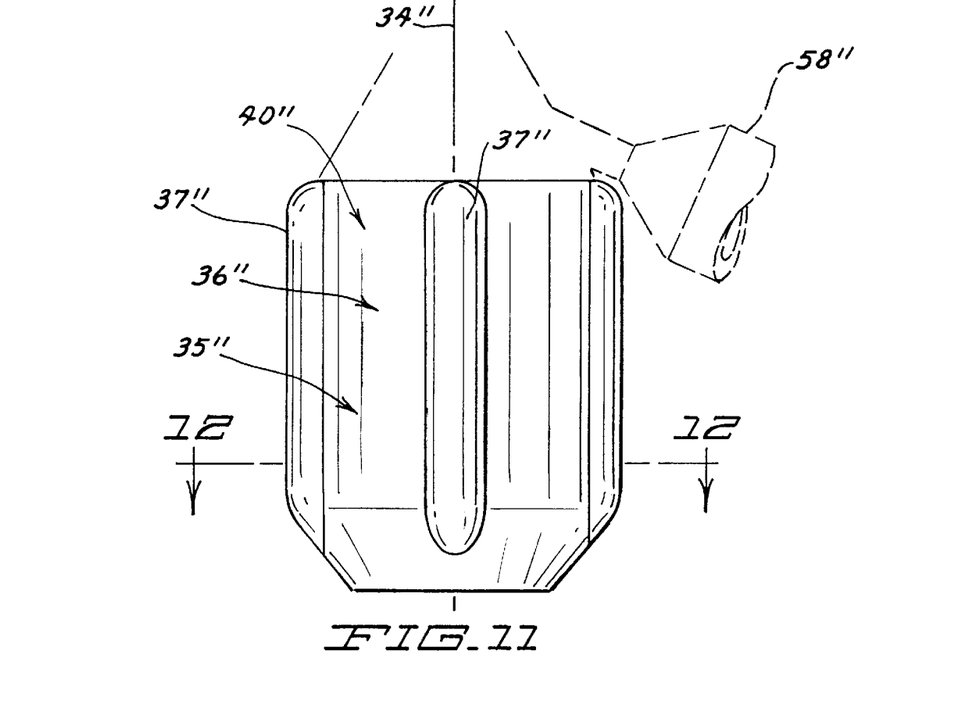
FIG. 11 is a side view of a alternate valve body.
Figure 12:
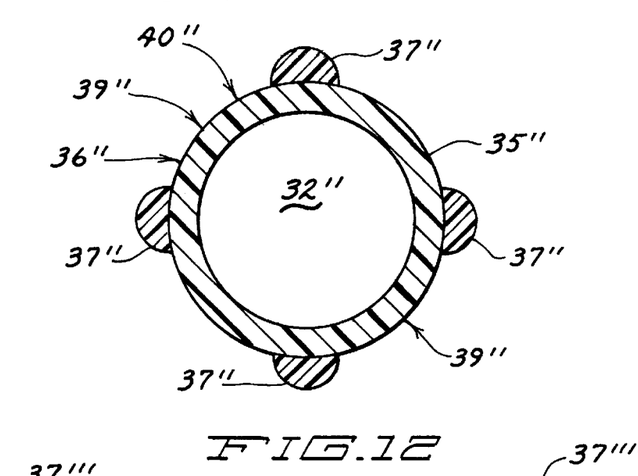
FIG. 12 is a cross-sectional view of the alternate valve body shown in FIG. 11 as seen from the line 12—12 of FIG. 11.
Figure 13:
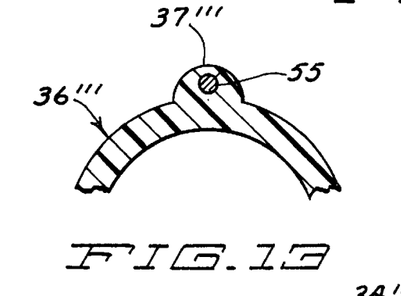
FIG. 13 is a partially broken away cross-sectional view of an alternate embodiment of the valve body shown in FIG. 11 as seen from a line similar to line 12—12 of FIG. 11.

Referring now also to FIGS. 9 and 10, the placement of the membranes or members 38 and 38' can be compared. In the embodiments represented in FIGS. 8 and 9, the valve membrane 38' is interconnected to the valve wall 40' generally proximate a midpoint between the respective proximal and distal shoulders 37' designated by dashed line 61'. When force is applied to opposite sides of valve 36', it is believed that valve membrane 38' is forced together about its periphery, thereby forcing at least one of the valve openings 76 to open. It will be appreciated, however, that the valve membrane may be removed from this midpoint to improve the ease with which one might open the valve. For example, a preferred embodiment of the valve 36, is shown in FIGS. 4–7 and 10, as a valve membrane 38 which is interconnected with the valve wall 40 in a position removed from such a lowest point in the depression located midway between the respective proximal and distal protective shoulders 37 as cited by dashed line 61. In this embodiment, when force is applied on opposite sides of the valve 36 at this lowest point in the depression, in which ones' fingers will naturally gravitate, will enable the user to open the valve 36 and at least one of its valve openings 76 with greater ease because the application of force at this point is respect to this particular embodiment, advantageously utilizes a greater portion of the valve wall 40 as a lever arm to pivot the leaflet 80 upward and away from the remainder of the valve membrane 38. In this way, the leaflet 80 is cantilevered so that the leaflet 80 pivots generally proximate the interconnection between the valve wall 40 and the valve membrane 38, rather than being pressed inward to the degree to which it is believed to move in the alternate embodiment shown in FIGS. 8 and 9.

Figure 14:
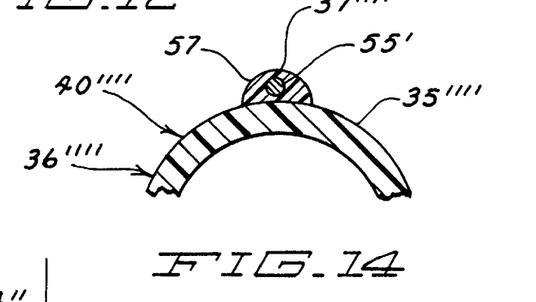
FIG. 14 is a partially broken away cross-sectional view of a further alternate embodiment of the valve body and shown in FIG. 11 as seen from a line similar to line 12—12 of FIG. 11.

Referring now also to FIGS. 11–14, further embodiments of the present multi-axial palpitatable discharge valve 36", 36''' and 36"". In the embodiment shown in FIGS. 11 and 12, raised protective shoulders 37" are provided by attaching bars of a second material different, from the first material used to form the valve wall 40', to the outer surface of the valve wall to provide rigidity to valve 36" so as to minimize inadvertent releases of urine caused by accidental application of force to opposite sides of the valve 36'. The second material used to make the bars or ridges which create the raised protective shoulders 37" may be made of any material which has a greater rigidity or "hardness" than the first material used to form the valve wall 40". Preferably this material will be a polymeric which is easily secured or bonded to the outer surface 35" of the valve wall 40" using techniques which are well known in the art. The bars used to create the raised ridges 37" are generally aligned with the longitudinal axis 34" of the valve 36". Alternatively, a metal bar 55 or other rigid material of the type mentioned herein before may be incorporated into a raised protective shoulder 37''' as shown in the alternate embodiment shown in FIG. 13. In this embodiment, the second material 55 may be incorporated into the raised protective shoulder 37''' during a molding process or may be inserted subsequent to creation of the valve body 36''' if an opening for insertion of the second materially 55 is provided. As shown in FIG. 14, a similar structure 37"" can be created by attaching a rigid bar or a ridge 37"" to the outer surface 35"" of a molded valve wall 40"" which is made of a second material 57 and can contains a reenforcing rod or bar 55'. In each of these cases, it will be appreciated that the shape, size and makeup of the respective reenforcing structures can be varied to adopt virtually any configuration in which effectively provides rigidity to minimize unintended valve opening resulting from accidental application of force to the outer surface of the valve body.

The inflatable balloon 18 is fixedly and sealingly attached to the catheter body 12 using an adhesive bond between a predetermined portion of the exterior surface of the catheter body 12. In preferred embodiments made of silicone rubber, the adhesive is a Q74840 two-part medical grade silicone adhesive from Dow Chemical Co. in Midland, Mich.

In preferred embodiments of the present catheter 10, the inflatable balloon 18 has either a generally spheroidal or generally toroidal shape in which the thickness of the side walls of the inflatable balloon 18 is substantially uniform along each path circumscribing the inflatable balloon 18 formed at each axial segment along the longitudinal length of the inflatable balloon 18, and over the entire surface area of the inflatable balloon 18, such that the inflatable balloon 18 is uniformly and symmetrically shaped and disposed in radial symmetry relative to the longitudinal axis 34 of the catheter body 12.

Referring now specifically to FIGS. 4 and 5, it will be appreciated that the injection port 58 is preferably fabricated by inserting or receiving a conventional Halkey-Roberts type valve into a molded retainer attached in fluid communication with the intermediate tube 56 and inflation lumen 52. The Halkey-Roberts type valve may have the retainer molded around the exterior thereof, or the Halkey-Roberts type valve may be pressure fit within the retainer and secured in place by an annular projection that engages within a corresponding groove defined by the interior of the retainer. A self-sealing silicone valve may also be utilized in place of the Halkey-Roberts type valve to enhance the aesthetic appearance and reduce the size of the exposed portions of the particular catheter 10. However, care must be taken not to puncture or damage the self-sealing valve or the entire catheter 10 is rendered useless.

The inflation lumen 52 can be molded as an integral part of the catheter wall 26 in the proximal portion 16 of the catheter body 12 by inserting a removable wire within the mold along the predetermined path of the inflation lumen, or can be fabricated by placing a corresponding diameter tube within the mold extending between the position of the opening 54 and the injection port 58. The intermediate tube 56 preferably exits the proximal portion 16 of the catheter body 12 at an angle relative to the longitudinal axis 34 and proximal to the seam between the distal portion 14 and proximal portion 16 of the catheter body 12, as to permit fabrication and cutting of the valve 36 as a separate component, and to prevent the intermediate tube 56 or injection port 58 from interfering with the palpitation of the discharge valve 36 or the discharge of urine from the discharge opening 32. It will further be appreciated that the valve openings 76 are preferably cut through the valve member 38 prior to the distal portion 14 of the catheter body being engagingly mounted and bonded (or otherwise fixedly attached) to the proximal portion 16 of the catheter body 12 to form a complete unitary catheter 10.

Referring now particularly to FIG. 1, it will be appreciated that the retention collar 20 is molded as a separate unit and mounted on the catheter body 12 prior to insertion of the catheter body 12 within the patient. The collar 20 may be mounted either before or after the distal end 46 of the inflatable balloon 18 has been secured to the catheter body 12, but prior to its inflation. The relative position of the collar 20 along the length of the catheter body 12 is adjusted by rotating the collar 20 relative to the catheter body 12. With helical threads 60 having a constant and uniform pitch, the axial movement of the collar 20 relative to the catheter body 12 will be generally proportional to the relative number of revolutions or the degree of angular rotation between the collar 20 and catheter body 12. Rotation in one direction will move the collar 20 proximally along the catheter body 12, and rotation in the opposite direction will move the collar distally.

While the direction of relative rotation of the retention collar 20 may be selected as desired, it is deemed advantageous to have a collar 20 move proximally when the catheter body 12 is gripped by the left hand adjacent the valve 36 and the collar 20 is rotated clockwise by the right hand. It will be appreciated that a collar 20 will not be used in all applications, and will preferably be utilized with female patients, because female patients generally have shorter urethral lengths and greater need for supplemental anchoring or protection against jarring or displacement of the inflatable balloon 18 when drawn against the neck and orifice of the bladder to prevent urine leakage around the catheter.

Referring now particularly to FIGS. 1 and 2, the catheters 10 and 10' of this invention are shown implanted in a conventional manner within the bladder 124 and urethra of a female and male patient, respectively. It will be appreciated that in a male patient, the use of a collar 20 is not as likely to provide a suitable option for tensioning the catheter body 12 and inflatable balloon 18. One alternative to the use of a collar 20 is an inflatable member (not shown) disposed adjacent to the exterior of the bladder 124, and another option is to increase the length of the catheter 10 to provide sufficient excess catheter body 26 external to the patient to minimize dislodgement.

Due to the natural permeability of the silicone material from which the preferred inflatable balloon 18 is formed, the fluid (usually physiological saline) used to inflate the inflatable balloon 18 may be treated with an aliquot of a therapeutic agent bactericidal or microbicidal agent that will diffuse through the inflatable balloon 18 into contact with urine within the bladder 124, or alternately will contact urine which diffuses through and into the interior of the inflatable balloon 18. Instead of a bactericidal agent, other therapeutic compounds could be utilized, such as steroids, anti-inflammatory agents, or other medications designed to treat specific conditions.

In addition, because infections tend to migrate or gravitate up the catheter body 12 and urethra toward the bladder 124, the bore and proximal face of the collar 20 and surrounding portion of the catheter body 12 may be coated with an anti-bactericidal or anti-microbicidal agent 63 in a gel or liquid form. Alternately, the material from which the catheter body 12 is fabricated may be impregnated with a predetermined concentration of a bactericidal agent such as silver. The catheter body 12 may also be coated with friction-reducing agent such as Teflon®, a silicone having a different durometer hardness than the catheter body 12, or various other biocompatible materials selected for their known and intended physiological properties.

In a representative embodiment for female patients as shown in 2, the catheter 10 has an overall length of between about 4" and 5" measured between the proximal end 28 and distal end 30, and the inflatable balloon 18 has a relaxed wall thickness of 0.010" compared to a wall thickness for the catheter body of 0.035". The helical threading 60 has alternating lands and grooves, with lands of 0.040" width separating ovoid section grooves having a width of 0.040" and a depth of 0.020" or slightly greater. It will be readily appreciated that the dimensions of the various components of the catheter 10 will be determined based upon conventional anatomical measurements, and various sizes and shapes for these components will be required to accommodate patients with different anatomical characteristics.

Each element or component of the catheter 10 is preferably fabricated from a synthetic material such as biologically compatible such as silicone, Kraton®, and the like, and assembled using an appropriate biologically compatible adhesive that withstands the temperature and exposure to bodily fluids associated with an indwelling catheter 12 that is used for extended periods of time. Suitable adhesives are known to the art and their selection is a matter of simple design choice. When silicone is selected as the material for molding the catheter body 12 and inflatable balloon 18, a durometer hardness of about 50 for the balloon inflatable 18, about 70 for the catheter body 12, and about 45–70 for the valve 36 have proven suitable.

Due to the pliability of the materials used to fabricate the catheter 10, a removable reinforcing member (not shown) in the form of a generally straight rod or tube having a radiused tip that is received within the central lumen 22 may be require to provide sufficient stiffness or rigidity to permit insertion of the catheter 10.

A wide variety in the selection of valves 36 and valve member 38 configurations, tolerances, dimensions, hardness, materials, and adhesives compared to the representative examples shown and discussed above can be made by those of ordinary skill in the art when fabricating and assembling a urinary catheter 10 according to the teachings set forth herein.

Figure 7:
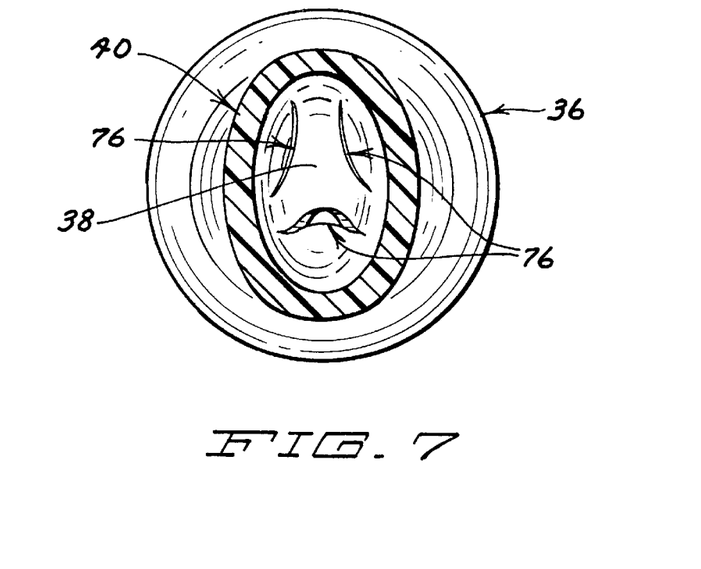
FIG. 7 is a cross-sectional view of the upper portion of discharge valve similar to the shown in FIG. 5, but showing the valve in the open position shown in FIG. 6.

The preferred valve member 38 has three curved valve openings 76. The respective edges of valve openings 76 define three intermediate ribs 78 connected to one another in a central location to form a Y-shape and separating three valve segments 80 from one another. When the valve wall 40 is squeezed radially inward from any two diametrically opposing sides, such as shown by the hollow arrows in FIG. 6, the valve wall 40 and valve member 38 are deformed substantially from the closed configuration shown in FIGS. 4 and 5 to an open configuration as shown in FIGS. 6 and 7. At least one element 80 of the arcuate dome 38 flexes proximally or upstream, and the boundaries of the valve openings 76 defined by the contacting surfaces between the valve segments 80 and intermediate ribs 78 separate to create one or more openings through which fluid may flow from the interior of the valve 36 and the central lumen 22 to the discharge opening 32. When the radially inward pressure is released, the valve 36 returns to the closed configuration shown in FIGS. 4 and 5, with the edges or contact surfaces of the valve segments 80 contacting the closely conforming contact surfaces of the intermediate ribs 78 to maintain proper alignment and closure of the valve openings 76 without the valve segments 80 overlapping or being axially displaced from the intermediate ribs 78 so as to present a gap through which fluid can pass.

The cuts or slits through the valve member 38 forming the valve openings 76 extend from the highest respective point on the apex 66 of the valve member arcuate 38 downwardly or distally and intersect with a portion of the peripheral edge 74 which demarks the lowest or most distal point upon the convex surface 70. These intersection points between the valve openings 76 and the peripheral edge 74 of the dome are disposed at or near the radial center of trough 75 in the intermediate region 68 at approximately the lowest or most distal point, with the entire upstream surface of the valve member 38 being disposed more proximal than those intersection points, thereby ensuring that when the valve openings 76 are in the open configuration the valve member 38 will not present any concave recesses disposed more proximal to the intersection points 82, and fluid within the interior of the valve 36 will drain completely through the valve openings 76 even though there is little or substantially no remaining fluid pressure.

It will be appreciated that a variety of surface configurations and non-uniform terrains may be utilized for the convex surface 70 and concave surface 72 of the valve member 38. However it is preferred that in any such configuration no portion of the upstream face of the trough 75 along the shortest path from an intersection point between the valve opening 76 and the peripheral edge 74 and the adjacent or most proximate portion of the valve wall 40 be disposed further downstream than that intersection point, thereby preventing an aliquot of fluid from being trapped in a recess or cavity rather than draining through the valve opening due to the force of gravity when the valve member 38 is deformed and the valve 36 is maintained in the open position. In this preferred embodiment, that arcuate segment or dome of the valve member 38 defines a generally uniform ovoid section extending downwardly to the peripheral edge 74, with the peripheral edge 74 defining a plane oriented generally perpendicular to the longitudinal axis 34 of the catheter body 12 within the interior region of the valve 36.

In addition, the slits defining the valve openings 76 may extend from the arcuate dome 38 across the peripheral edge 74 toward the interior surface of the side wall 40, but preferably not actually contacting or intersecting the interior surface of the side wall 40. In this manner, the width of the valve opening 76 is increased in the region directly adjacent to or surrounding the intersection points between the valve openings 76 and the peripheral edge 74 (representing the bottom-most point of the trough 75) compared with the width of a conventional valve opening 76 at the intersection with the side wall 40 of the valve 36. The result is to increase low-pressure drainage compared with conventional dome-type valves, and minimize the risk that the side wall 40 will be damaged during fabrication of the valve openings 76. This also increases the eventual maximum width of the valve openings 76 at the greatest distances from the side wall 40 when the dome 38 is fully deformed. Given a predetermined separation between the peripheral edge 74 of the valve member 38 and the side wall 40, the valve opening 76 could extend from the valve member 38 past the intersection points a distance on the order of one half that separation.

The valve openings 76 are preferably cut through the valve member 38 by inserting a radially oversized mandril (not shown) through the discharge opening 32 of the valve 36, thereby flexing the conical segment outward and stretching the valve wall 40 and valve member 38 radially outward and away from the longitudinal axis until the valve member 38 is in a generally planar or flat configuration. A cutting tool (not shown) having a blade member on its leading edge is inserted through the proximal opening in the distal portion 14 of the valve 36, and into close proximity to the valve member 38. Using opposing pressure exerted by the mandril to restrain the valve member 38 against axial movement, the blade member is forcibly pressed toward the mandril so that the blade member contacts and completely penetrates the valve member 38 and defines the particular pattern or configuration of valve openings 76 that is desired. The top surface of the mandril is preferably fabricated from a sufficiently compliant material such that the blade member may score the surface of the mandril to ensure complete penetration of the valve member 38. The cutting tool and mandril are removed from the interior of the valve 36, which is released from the stretched position so that the valve member 38 returns to its normally undeformed convoluted configuration as shown in FIG. 9. The truncated conical section of the valve 36 may initially be stretched to permit ingress of the mandril using a plurality of fingers (not shown) or other segments that are inserted within the valve 36 through the distal opening 32 and are separated to stretch the valve 36 sufficiently to permit passage of the mandril. The fingers or other segments may be removed during the cutting operation to maintain uniform radial tension o the valve member 38. In the deformed configuration, the valve member 38 may be stretched across the top and down the sides of the mandril, with the generally flat or planar section corresponding to the area of the valve member 38 within and defined by the peripheral edge 74 and encompassing the portion of the intermediate section 78 or the trough 75 disposed within the peripheral edge 74. In an embodiment where the valve openings 76 cross the peripheral edge 74 and extend beyond the lowest point of the trough 75, the mandril must be slightly larger than the diameter of the peripheral edge 74. It will be appreciated that the valve member 38 may not achieve a completely flat or planar configuration, since tension decreases proportionately to the proximity to the center point or longitudinal axis 34 of the valve member 38, however, the blade member presses the valve member 38 substantially flat prior to cutting.

In the three-element valve 36 with intermediate ribs 78 shown in FIGS. 4–7, the top valve member 38 deforms upwardly and is displaced a greater radial and axial distance than the intermediate ribs 78 or lower two valve elements 80. When pressure is released, the intermediate ribs 78 and lower two valve elements 80 return to their original closed configuration prior to the top valve element 80, which subsequently nests and seats properly against the intermediate ribs 78 as the valve element 80 moves radially and axially back into contact with the intermediate ribs 78.

The use of curved slits and intermediate ribs 78 produces a synergistic effect by providing a multi-axial valve 36 that will seat reliably and completely, and eliminating sharp corners that can overlap or catch due to poor memory in the adjacent portions of the valve elements 80.

It should be noted that the preferred valve 36 has been described herein as having a dome-type valve member 38, however this representative terminology can include a variety of other types of valve members 38 having corresponding shapes such as conical, truncated conical, oval or ovoid, pyramidal, trapezoidal. The common element among these configurations of valves 36 is their inclusion of an elevated region disposed more proximally and forming an apex 66, and a surrounding lower portion disposed more distally and forming a base or peripheral edge 74 which may gradually and uniformly transition into a trough 75.

While preferred embodiments of the urinary catheters 10 and methods of use and methods for manufacture of the same as currently contemplated have been described in detail with reference to the attached drawing Figures, it is understood that various changes and adaptations may be made in the urinary catheters 10 of the present invention and elements thereof, and to the elements of the inventive methods of use and manufacture described herein without departing from the spirit and scope of the appended claims.

What is claimed is:

1. An indwelling urinary catheter for use by a patient to manage urinary incontinence or retention, the patient having a bladder for retaining urine, the bladder communicating with a urethra, the catheter comprising:

(a) a catheter body defining both an exterior surface and interior surface, the interior surface defining a central lumen through which the urine can flow from the bladder when the catheter is inserted at least partially into the urethra; and (b) a discharge valve in fluid communication with the central lumen, the discharge valve having a valve body including a valve wall defining an outer surface, the discharge valve further including a valve membrane having at least one valve opening, the valve openings having both a closed and an open position, wherein the patient can selectively manipulate the valve such that the at least one valve openings can be opened from a closed position to allow urine to pass through the valve from the bladder and the central lumen, and be closed from an open position to restrain the flow of urine from the bladder through the central lumen, such that the valve can be manipulated by the patient from the closed position to the open position where the patient compresses opposite sides of the valve wall toward one another when engaging the outer surface of the valve wall, the outer surface having a plurality of protective shoulders, the plurality of protective shoulders including at least a pair of protective shoulders, each pair of protective shoulders being separated by an unprotected portion, the plurality of protective shoulders providing structural support to the valve wall such that each of the valve opening can remain in the closed position when a force is applied to the outer surface of the valve wall proximate any of the plurality of protective shoulders, which force would be sufficient to manipulate the valve such that at least one of the valve openings would be opened from a closed position if the force was applied to the unprotected portion of the valve wall, wherein the protective shoulders provide a measure of protection against an accidental opening of the at least one valve openings due the inadvertent application of a force to the outer surface of the valve wall.

2. The indwelling urinary catheter of claim 1 wherein the valve membrane is interconnected at its periphery to the inner surface of the valve wall and has a plurality of valve openings, the valve membrane being dome-shaped in a convex center portion and having trough generally encircling the convex center portion proximate the outer edge or periphery, wherein the upper surface of the valve membrane proximate the trough is further distally removed from proximal portions of the catheter body than the upper surface proximate the convex center portion, each of said plurality of valve openings being an elongated slit in the valve membrane which passes through both the upper and lower surfaces of the valve membrane.

3. The indwelling urinary catheter of claim 2 wherein the valve is multi-axial such that at least one of said plurality of valve openings can be manipulated by the patient from a closed position to an open position when the patient compresses opposite sides of the valve wall together when engaging the outer surface of the valve wall.

4. The indwelling urinary catheter of claim 1 wherein the plurality of protective shoulders are raised above the unprotected portions of the outer surface of the valve wall and provide structural support to the valve wall such that the valve wall can resist a force applied to the outer surface proximate any of the plurality of raised protective shoulders, which force would be sufficient to manipulate the valve such that at least one of the valve openings can be opened from a closed position if the force is applied to an unprotected portion of the valve wall, wherein the protective shoulders provide a measure of protection against an accidental opening of one of the valve openings due the inadvertent application of a force on the outer surface of the valve wall.

5. The indwelling urinary catheter of claim 1 wherein the valve wall and the valve membrane are substantially made of a first material which is a flexible polymeric material which can be deformed such that the valve openings can be opened from a closed position when sufficient force is applied the valve wall to deform the valve membrane, wherein the valve opening will generally return to the closed position from the open position when the force is no longer applied, the valve wall including an elongated thickness of a second material proximate each of the plurality of protective shoulders, the second material being more rigid than the first material such that the second material is more resistant to deformation than the first material.

6. The indwelling urinary catheter of claim 3 wherein the second material is stainless steel.

7. The indwelling urinary catheter of claim 3 wherein the second material is a hard plastic.

8. The indwelling urinary catheter of claim 3 wherein the second material is a flexible polymeric material having a greater hardness than the first material.

9. The indwelling urinary catheter of claim 1, at least one of said plurality of valve openings having an arcuate shape, the elongated slit passing from a first location proximate the trough on the upper surface, to a second location closer to an apex of the convex center portion relative to the first location, and then to a third location more removed from the apex of the convex center portion as compared to the second location, wherein there are at least two valve openings having an arcuate shape and the respective elongated slits pass from said first location, to said second location, to said third location.

10. The indwelling urinary catheter of claim 1 wherein the catheter has an inflation lumen and an inflatable retention balloon, said retention balloon being axially symmetrical with respect to the catheter body.

11. The indwelling urinary catheter of claim 1 wherein the catheter body has a threaded area on its exterior surface and a retention collar engaged around the catheter body proximate the threaded area, the threaded area providing helical threading disposed along a portion of the exterior surface of the catheter body, the retention collar having mated threading disposed within a bore of the collar such that the collar can be mounted on the catheter body in threaded engagement therewith.

12. The indwelling urinary catheter of claim 9 wherein the hardness of the catheter and elements thereof, as measured by durometer measurements, differs in that the balloon has a lower durometer than other portions of the catheter and the valve.

13. The indwelling urinary catheter of claim 1 wherein the discharge valve has a discharge opening at the distal end of the valve and a drainage tube connector can be inserted into and engaged within the discharge opening such that the connector engages the lower surface of the valve membrane so that the membrane is deformed and the valve membrane can be deformed such that the valve openings remain in an open position when the valve membrane is so engaged.

14. In a catheter for use by a patient to control urinary incontinence or retention, said patient having a bladder for retaining urine and a urethra in fluid communication with the bladder, the urethra having a distal end, said catheter comprising:

a catheter body to be disposed at least partially within said urethra of said patient, said catheter body defining a lumen through which urine flows from said bladder to said distal end of said urethra when the catheter body is so disposed, a valve connected to said catheter body in fluid communication with said lumen such that said patient can selectively manipulate said valve between a closed position and an open position to void urine from the bladder through said lumen, said valve including a valve body having a valve wall defining an outer surface, an interior region, an inner surface, and a valve membrane connected to said valve wall and disposed within said interior region, the valve membrane having a generally arcuate segment defining a generally convex surface, a generally concave surface, and a peripheral edge, said convex surface of said valve membrane being oriented facing generally upstream opposing the flow of urine through the valve body, the valve membrane further defining a first valve opening and a second valve opening each extending entirely therethrough and disposed in fluid communication with the lumen, the valve membrane being generally deformable when the patient selectively manipulates the valve so as to permit the flow of urine through said first valve opening or said second valve opening or both, the valve membrane including a first segment, a second segment, and a rib member, at least a portion of said rib member being disposed between and contacting both said first segment and said second segment of said valve membrane when the valve is closed, said first segment or said second segment or both being displaced a distance apart from said rib member when said valve membrane is deformed, the outer surface having a plurality of protective shoulders which provide structural support to the valve wall such that each of the valve openings can remain in the closed position when a force is applied to the outer surface of the valve wall proximate any of the plurality of protective shoulders, which force would be sufficient to manipulate the valve such that at least one of the valve openings would be opened from a closed position if the force was applied to an unprotected portion of the valve wall, wherein the protective shoulders provide a measure of protection against an accidental opening of one of the valve openings due the inadvertent application of a force to the outer surface of the valve wall, wherein the plurality of protective shoulders are raised above the unprotected portions of the outer surface of the valve wall and provide structural support to the valve wall such that the valve wall can resist a force applied to the outer surface proximate any of the plurality of raised protective shoulders.

15. The catheter of claim 14 wherein the first segment, the second segment, and the rib member of the arcuate segment of the valve membrane are integral with one another.

16. The catheter of claim 14 wherein the first segment, the second segment, and the rib member of the arcuate segment of the valve membrane are formed integrally with one another.

17. The catheter of claim 14 wherein the first valve opening and the second valve opening are separated from and do not intersect one another, and wherein the first segment, the second segment, and the rib member of the arcuate segment of the valve membrane are a fabricated as one piece.

18. The catheter of claim 14 wherein the first segment of the valve membrane defines a first surface contacting the rib member when the valve is in the closed position, and the second segment of the valve membrane defines a second surface contacting the rib member when the valve is in the closed position, said first surface of the first segment and said second surface of the second segment not contacting one another when the valve is in the closed position.

19. The catheter of claim 14 wherein the first valve opening does not intersect the second valve opening.

20. The catheter of claim 14 wherein the valve membrane defines a third segment and a third valve opening, at least a second portion of the rib member being disposed between and contacting both the first segment and said third segment of the valve membrane when the valve is closed, at least a third portion of the rib member being disposed between and contacting both the second segment and said third segment of the valve membrane when the valve is closed.

21. The catheter of claim 20 wherein the third segment of the valve membrane defines a third surface contacting the rib member when the valve is in the closed position, said third surface of the third segment not contacting either the first surface of the first element or the second surface of the second element when the valve is in the closed position.

22. The catheter of claim 20 wherein the third valve opening does not intersect either the first valve opening or the second valve opening.

23. The indwelling urinary catheter of claim 5 wherein the elongated thickness of the second material is a bar extending along the valve wall generally parallel with the central lumen of the catheter.

24. The indwelling urinary catheter of claim 5 wherein each of the protective shoulders generally include the valve.

25. The indwelling urinary catheter of claim 24 wherein the elongated thickness of the second material is ring encircling the valve.

* * * * *